United States Patent [19]

De Vincentiis

[11] Patent Number: 4,496,589
[45] Date of Patent: Jan. 29, 1985

[54] ANTI-INFLAMMATORY, DISINFECTANT AND ANTI-BACTERIAL COMPOUND

[75] Inventor: Leonardo De Vincentiis, Rome, Italy

[73] Assignee: Ausonia Farmaceutici s.r.l., Rome, Italy

[21] Appl. No.: 439,067

[22] Filed: Nov. 4, 1982

[30] Foreign Application Priority Data

Nov. 26, 1981 [IT] Italy .................... 25298 A/81

[51] Int. Cl.³ .............. C07C 143/63; C07C 129/08; A61K 31/155
[52] U.S. Cl. .................. 514/565; 514/632; 260/501.14; 562/466
[58] Field of Search ............ 260/501.14; 424/326, 424/199, 319; 562/466

[56] References Cited

U.S. PATENT DOCUMENTS

| | | | |
|---|---|---|---|
| 3,183,230 | 5/1965 | Shapiro | 424/326 |
| 3,468,898 | 9/1969 | Cutler et al. | 424/326 |
| 3,980,699 | 9/1976 | Fried et al. | 562/466 |
| 4,009,197 | 2/1977 | Fried et al. | 562/466 |
| 4,022,834 | 5/1977 | Gundersen | 424/326 |
| 4,198,392 | 4/1980 | Juneja | 424/326 |
| 4,207,241 | 6/1980 | Fried et al. | 562/466 |
| 4,268,442 | 5/1981 | Kondo et al. | 562/466 |

Primary Examiner—Glennon H. Hollrah
Assistant Examiner—Raymond Covington
Attorney, Agent, or Firm—Bucknam and Archer

[57] ABSTRACT (+)-6-methoxy-α-methyl-2-naphthalene acetate of N,N''-bis (4-chlorophenyl)-3,12-diimino-2,4,11,13-tetraazatetradecan-diimidoamide, possessing the formula (I)

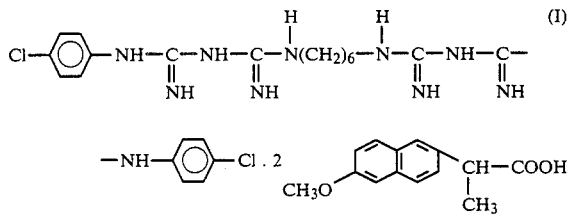

has high bioavailability by the cutaneous route which enables it to be used topically for the treatment of dermatoses, infected wounds, scalds, bedsores, inflammations of the oral cavity, vulvovaginitis, etc.

3 Claims, No Drawings

ANTI-INFLAMMATORY, DISINFECTANT AND ANTI-BACTERIAL COMPOUND

The present invention relates to a new compound with anti-inflammatory, disinfectant and anti-bacterial activity, viz. (+)-6-methoxy-α-methyl-2-naphthalene acetate of N,N''-bis (4-chlorophenyl)-3,12-diimino-2,4,11,13-tetraaza-tetradecan-diimidoamide, possessing the formula (T)

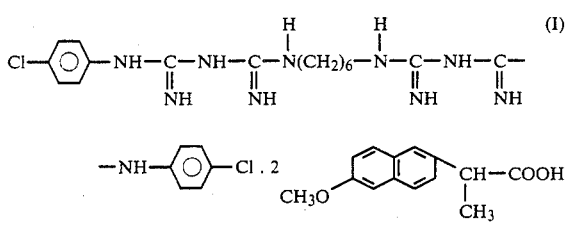

The invention also provides a process for the preparation of compound (I), and pharmaceutical compositions for topical use containing the said compound at the active principle.

It is known that N,N''-bis(4-chlorophenyl)-3,12-diimino-2,4,11,13-tetraaza-tetradecan-diimidoamide (better known as chlorhexidine) is endowed with marked disinfectant activity (see, inter alia, U.S. Pat. No. 2,684,924). The anti-inflammatory properties of (+)-6-methoxy-α-methyl-2-naphthyl acetic acid, or naproxen (U.S. Pat. No. 3,637,767) are also known.

It has now unexpectedly been found that compound (I) (chlorhexidine dinaproxenate) has, in addition to foreseeable anti-inflammatory, disinfectant and anti-bacterial properties, a surprisingly high bioavailability by the cutaneous route, which allows particularly effective topical use of the compound.

According to the present invention, this compound is prepared by reacting chlorhexidine and naproxen (in a molar ratio substantially equal to 1:2) in suspension in solvents preferably consisting of $C_1$-$C_4$ alcohols, possibly containing a small proportion of water, at temperatures between about 10° and about 100° C., preferably at the solvent's boiling point. When the solution so obtained is cooled, salt (I) is precipitated in crystalline form and is isolated and where necessary recrystallised in known manner.

The following example illustrates the process procedure without limitation.

EXAMPLE 40 grams of chlorhexidine are heated under reflux in 600 ml of ethanol; 36.5 g of naproxen suspended in 400 ml of ethanol are added to the suspension. Immediate solubilization of all the suspended material is obtained, therefore heating is discontinued and it is left to cool at ambient temperature, with stirring. It is pumped through a filter, obtaining 70 g of crystalline product with a melting point of 146°-148° C.

Compound (I) so obtained which will hereinafter be designated by the reference AF 504, for the sake of brevity, is difficulty soluble in water and the common organic solvents but dissolves in dimethyl sulphoxide even when cold.

Quantitative analyses: for $C_{50}H_{58}Cl_2N_{10}O_6$ (molecular weight=965.98): % calculated: C=62.17; H=6.05; N=14.50; % found: C=62.03; H=6.09; N=14.42

I.R. spectrum (Nujol mull): 3600-2650 $cm^{-1}$ (extended bands O—H, N—H); 1640 $cm^{-1}$ (C=O); 1610 $cm^{-1}$(C=C); 1580 $cm^{-1}$ (C=N).

$^1H$ NMR spectrum (recorded in hexadeuterodimethyl sulphoxide, internal ref. TMS): 1.5 δ (d, 3H, CH—$\underline{CH_3}$); 1–1.7 δ(m, 12H, HN—$\underline{(CH_2)_6}$—NH; 3.65 δ(9, 1H, e,uns/CH/ —$CH_3$); 3.9 δ(s, $\underline{3H}$, $OCH_3$); 7-8.5 δ (aromatic m, 14H and mobile NH).

Pharmaco-toxicological examination of AF 504 has led to the results set out below.

Toxicity: the LD50 was determined in the mouse by the oral route and proved to be 1650 mg/kg.

Cutaneous tolerance tests: topical tolerance of AF 504 was determined by the rabbit eye irritation experimental pattern, observing the effects produced by the application of AF 504 to the cornea, the iris and the bulbar and palpebral conjunctiva.

0.1 ml of a 5% aqueous suspension of AF 504 caused slight eye irritation in the cornea only, producing slight opacity, which disappears quickly after washing the eye with water. In the test used, therefore, AF 504 shows good topical tolerance.

Anti-bacterial activity: AF 504's anti-microbial activity was tested on the following micro-organisms, using the diffusion on agar method:

Gram-positive bacteria:
*Staphylococcus aureus*
*Streptococcus faecalis* ATCC 10541
*Staphylococcus epidermis* ATCC 1222
*Bacillus subtilis* (spore) ATCC 663

Gram-negative bacteria:
*Escherichia coli* serum type 0122/K71
*Pseudomonas aeruginosa* ATCC 27853
*Proteus vulgaris* ATCC 9920
*Salmonella enteritidis* CCB-V73

Yeasts:
*Candida albicans* IJFM

Fungi:
*Aspergillus niger*

Equimolecular solutions of AF 504 and chlorhexidine acetate were used, the latter as a comparative drug.

The two products are equally highly active on almost all the germs tested; both show reduced activity on Candida albicans and almost none on Asperigillus niger.

Anti-inflammatory activity

AF 504's anti-inflammatory activity was determined using the following experimental patterns:

oedema of the hind leg of the rat, carrageenin-induced;
UV ray-induced erythema in the guinea-pig.

Carrageenin-induced oedema of the hind leg of the rat

AF 504's anti-inflammatory activity was determined in the rat using this experimental pattern, administering both the compound under study and the comparative drug (Naproxen and Ibuprofen) by the oral route at the following doses:

AF 504 and Ibuprofen: 100 mg/kg
Naproxen: 50 mg/kg

The results set out in Table 1 show the anti-inflammatory activity of the three compounds to be practically superimposable (obtained in the case of Naproxen with a dose equal to half of that of the other two products).

UV-induced erythema in the guinea-pig

The guinea-pig flank was shaved and on part of it were applied AF 504, the comparative drug (Naproxen) and, for control purposes, the same cetylic base used as a carrier for the two drugs. After exposure to UV rays, the temperature differences between the treated area (Tt) and the untreated area (Tc) were recorded at successive times, viz. 2½, 3, 4, 5 and 24 hours after application of the products.

Both AF 504 and Naproxen were incorporated in the excipient at a concentration of 5%. The differences between Tc (temperature of the untreated area) and Tt (temperature of the treated area) decrease regularly in time and show that it is probably more a matter of delayed appearance of the erythematous effect than true inhibition.

The results set out in Table 2 indicate AF 504's activity to be greater; the comparison with Naproxen is the more significant because the two compounds were used at equiponderal but not equimolecular doses.

TABLE 1

| | | VOLUME OF THE LEG AT THE | | | | | | AREA | |
|---|---|---|---|---|---|---|---|---|---|
| | DOSE | VARIOUS TREATMENT TIMES | | | | | | | % v. |
| TREATMENT | mg/Kg p.o. | 0 | 1 h | 2 h | 3 h | 4 h | 5 h | absolute value | controls |
| CONTROLS | — | 23,6 | 35,7 | 40,0 | 39,0 | 42,0 | 42,8 | 305,5 ± 9,34 | — |
| IBUPROFEN | 100 | 22,8 | 31,7 | 31,4 | 28,9 | 33,0 | 33,2 | 169,8 ± 15,30 | −44,0 |
| NAPROXEN | 50 | 25,2 | 30,2 | 32,6 | 30,3 | 33,5 | 34,5 | 120,7 ± 13,45 | −60,0 |
| AF 504 | 100 | 24,9 | 31,0 | 31,9 | 32,2 | 34,7 | 35,0 | 140,1 ± 15,20 | −54,0 |

TABLE 2

| | | UV-induced erythema in the guinea-pig | | | | |
|---|---|---|---|---|---|---|
| | | (Tc − Tt)°C. | | | | |
| | Concentration | 2½ | 3 | 4 | 5 | 24 |
| Controls (excipient) | 5% | 0,01 ± 0,02 | 0,03 ± 0,02 | 000 ± 000 | 0,03 ± 0,02 | 000 ± 000 |
| Naproxen | 5% | 0,3 ± 0,06 | 0,27 ± 0,04 | 0,35 ± 0,03 | 0,3 ± 0,06 | 0,05 ± 0,03 |
| AF 504 | 5% | 0,45 ± 0,04 | 0,37 ± 0,02 | 0,5 ± 0,06 | 0,42 ± 0,07 | 0,18 ± 0,03 |

The invention also refers to all the aspects of industrial application connected with the use of AF 504 as an anti-inflammatory, disinfectant and anti-bacterial agent, in particular for the treatment of dermatosis with the threat or existence of infective complications; infected wounds; scalds; bedsores; inflammations of the oral cavity with an infective component, gingivitis, aphthae; vulvovaginitis, exocercivitis; and for personal hygiene during the puerperium. Consequently, an essential aspect of the invention consists of pharmaceutical formulations for topical use, containing predetermined quantities of AF 504. By way of example, the following formulations can be mentioned:

(a) dermatological creams;
(b) collutories;
(c) dermatological lotions;
(d) suspensions for gynaecological use;
(e) dusting powders;

all containing 1 to 10%, preferably 2–5%, of AF 504 together with the carriers, excipients, adjuvants, dispersants, etc., usually employed in pharmaceutical methods.

I claim:

1. The compound, (+)-6-methoxy-α-methyl-2-naphthalene acetate of N,N''-bis(4-chlorophenyl)-3,12-diimino-2,4,11,13-tetraaza-tetradecan-diimidoamide possessing formula (I):

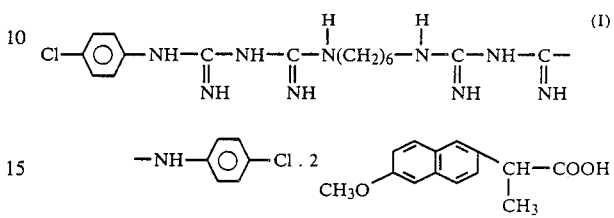

2. Pharmaceutical compositions, for topical use having anti-inflammatory, disinfectant and anti-bacterial activity, containing 1–10% by weight of (+)-6-methoxy-α-methyl-2-naphthalene acetate of N,N''-bis(4-chlorophenyl)-3,12-diimino-2,4,11,13-tetraazatetradecan-diimidoamide possessing formula

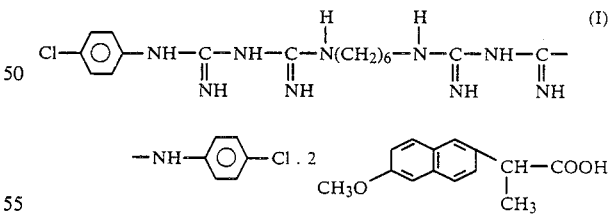

and at least one member selected from the group consisting of carriers, excipients, adjuvants and dispersants.

3. Pharmaceutical compositions according to claim 2 in the form of creams, lotions, collutories, suspensions, dusting powders.

* * * * *